United States Patent
Ries et al.

(10) Patent No.: US 7,225,034 B2
(45) Date of Patent: *May 29, 2007

(54) MEDICAL LEAD ADAPTOR

(75) Inventors: Andrew J. Ries, Lino Lakes, MN (US); Timothy W. Holleman, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 532 days.

This patent is subject to a terminal disclaimer.

(21) Appl. No.: 10/620,710

(22) Filed: Jul. 16, 2003

(65) Prior Publication Data

US 2004/0260373 A1 Dec. 23, 2004

Related U.S. Application Data

(63) Continuation-in-part of application No. 10/465,158, filed on Jun. 19, 2003.

(51) Int. Cl.
*A61N 1/05* (2006.01)

(52) U.S. Cl. ...................... 607/122; 607/119
(58) Field of Classification Search .................. 607/36, 607/37, 116, 119
See application file for complete search history.

(56) References Cited

U.S. PATENT DOCUMENTS

| | | | |
|---|---|---|---|
| 4,142,532 A | 3/1979 | Ware | |
| 4,182,345 A | 1/1980 | Grose | |
| 4,393,883 A * | 7/1983 | Smyth et al. | 607/123 |
| 4,628,934 A | 12/1986 | Pohndorf et al. | 128/419 PG |
| 5,070,605 A | 12/1991 | Daglow et al. | |
| 5,328,442 A * | 7/1994 | Levine | 600/17 |
| 5,514,161 A | 5/1996 | Limousin | 607/9 |
| 5,766,042 A | 6/1998 | Ries et al. | |
| 6,212,434 B1 * | 4/2001 | Scheiner et al. | 607/123 |
| 6,466,824 B1 | 10/2002 | Struble | 607/115 |
| 6,505,082 B1 * | 1/2003 | Scheiner et al. | 607/123 |
| 6,901,289 B2 * | 5/2005 | Dahl et al. | 607/9 |
| 2002/0103522 A1 * | 8/2002 | Swoyer et al. | 607/116 |
| 2003/0077943 A1 | 4/2003 | Osypka | |
| 2004/0064176 A1 * | 4/2004 | Min et al. | 607/126 |

FOREIGN PATENT DOCUMENTS

| | | |
|---|---|---|
| EP | 0 599 567 | 1/1994 |
| WO | WO 00/11762 A1 | 2/2000 |
| WO | WO 03/035173 A1 | 1/2003 |

OTHER PUBLICATIONS

Product List, Guidant Corporation, "Pacing and Defibrillation Toolkit" (Mar. 2003).
The Connector Task Force of the Pacemaker Committee, AAMI "Application Form for New Project," AAMI, p. 7 (Mar. 17, 2001).

* cited by examiner

*Primary Examiner*—Robert E Pezzuto
*Assistant Examiner*—Tammie K. Heller
(74) *Attorney, Agent, or Firm*—Michael C. Soldner; Carol F. Barry; Girma Wolde-Michael

(57) ABSTRACT

A medical electrical lead includes an electrode, a connector terminal and an auxiliary connector port, which includes a connector contact adapted to electrically couple an electrode of a second lead. A first connector element of the connector terminal is coupled to the electrode via a first insulated conductor, and a second connector element of the connector terminal is coupled, via a second insulated conductor, to the connector contact included in the auxiliary port.

18 Claims, 8 Drawing Sheets

MEDICAL LEAD ADAPTOR

This application is a continuation-in-part of application Ser. No. 10/465,158, filed Jun. 19, 2003.

FIELD OF THE INVENTION

The present invention relates generally to medical electrical leads and more particularly to means for connecting more than one medical lead terminal, each having a high-voltage contact, to a single connector port of an implantable medical device (IMD).

BACKGROUND OF THE INVENTION

In the field of therapeutic electrical stimulation, it is often desirable to provide electrical connection of more than one lead to a single connection port of a medical device. In particular, in the field of cardiac pacing, it is sometimes necessary to provide electrical connection of two leads to a single connection port of an IMD, e.g. a cardiac pacemaker or implantable cardioverter defibrillator, such that stimulation pulses may be delivered to more than one cardiac site or across a desired vector.

Medical lead connectors have been standardized in the industry. For example IS-1 pacing/sensing connectors are available in unipolar or bipolar configurations, including one or two electrical contacts, respectively, for making connection between a unipolar pace/sense electrode or a bipolar pace/sense electrode pair and an IMD; DF-1 connectors are available for making a high-voltage connection between an IMD and a defibrillation electrode via a single a single electrical contact. Other contemplated standards define connectors for making both high-voltage and low-voltage connections between an IMD and multiple electrodes; one such standard defines a connector including two high voltage contacts and two low voltage contacts, effectively combining two unipolar DF-1 connectors and a bipolar IS-1 connector into a single connector in order to provide electrical coupling to two high-voltage electrodes and a bipolar pace/sense electrode pair carried on a single, quadripolar lead for pacing and defibrillating the heart.

Clinical experience has shown that, in some patients, an acceptable defibrillation threshold cannot be reached using a single lead. In these patients, it becomes necessary to implant more than one lead in order to create an effective vector for the delivery of defibrillation energy. It is therefore desirable to provide means allowing connection of two connectors, each including a high voltage contact, to a single connector port of an IMD.

BRIEF DESCRIPTION OF THE DRAWINGS

Embodiments of the present invention will be more readily understood from the following detailed description when considered in conjunction with the drawings, in which like reference numerals indicate identical structures throughout the several views, and wherein.

The drawings are not necessarily to scale.

DETAILED DESCRIPTION OF THE INVENTION

Figure 1:
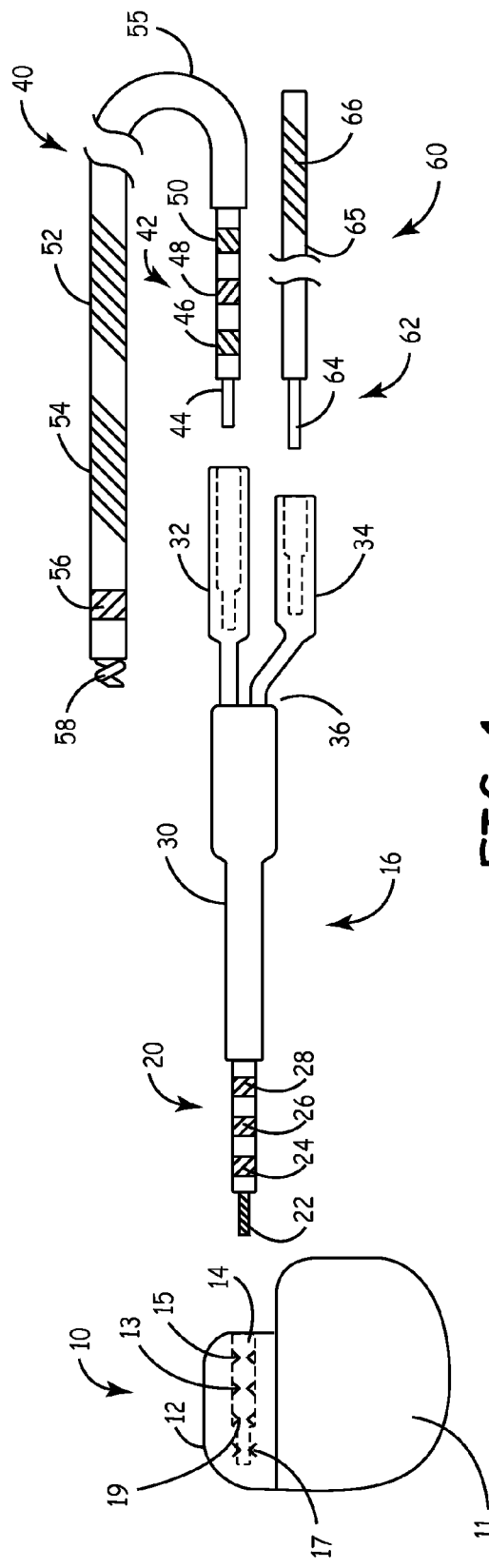
FIG. 1 is plan view of a medical system including a lead adaptor according to an embodiment of the present invention.

FIG. 1 is plan view of a medical system including a lead adaptor 16 according to an embodiment of the present invention. FIG. 1 illustrates the medical system including the adaptor 16 provided to couple a first lead 40 and a second lead 60 to an IMD 10. As illustrated in FIG. 1, first lead 40 includes a tip electrode 58 and ring electrode 56, which provide a low-voltage therapy, for example pacing and sensing, and two coil electrodes 52 and 54, which provide high-voltage therapy, for example defibrillation. Each electrode 52, 54, 56, and 58 is electrically connected to a corresponding connector element 50, 48, 46, and 44, respectively, located on a lead connector terminal 42 via electrically isolated conductors carried by a lead body 55. FIG. 1 further illustrates second lead 60 including a coil electrode 66 for high voltage therapy; electrode 66 is electrically connected to a connector pin 64 included in a lead connector terminal 62 via an insulated conductor carried by a lead body 65. According to embodiments of the present invention, if electrodes 54 and 52 of first lead 40, when implanted in a patient, cannot be positioned to provide an acceptable defibrillation threshold, electrode 66 of second lead 60 is implanted in a position where it may be employed to improve the threshold, and both first lead 40 and second lead 60 are coupled to a single connector port 14 of IMD 10 via adaptor 16.

Adaptor 16 includes a connector terminal 20 adapted to engage within connector port 14 of a connector header 12 of IMD 10, and, as illustrated in FIG. 1, connector terminal 20 includes three connector rings 24, 26 and 28 and a connector pin 22. Connector header 12 is shown attached to a hermetically sealed enclosure or can 11 that contains a battery and electronic circuitry and other components. Can 11 may further serve as a high voltage electrode in conjunction with lead electrodes 54, 52, 66. Port 14, configured to receive either first lead connector terminal 42 or adaptor connector terminal 20, includes high-voltage connectors 13 and 15 of any of the known types that are electrically connected to the electronic circuitry through feedthrough pins of feedthroughs (not shown) mounted to extend through can 11. Connectors 13 and 15 are dimensioned in diameter and are spaced apart in port 14 to receive and make electrical and mechanical connection with connector rings 26 and 28, respectively, of adaptor connector terminal 20, or with connector elements 48 and 50 of lead connector terminal 42. Such electrical and mechanical connection is effected either through the tightening of setscrews (not shown) as disclosed in U.S. Pat. Nos. 4,142,532 and 4,182,345, for example, or an action of inwardly extending force beams (not shown) as disclosed in U.S. Pat. Nos. 5,070,605 and 5,766,042, for example. Additional connectors 17 and 19 included in port 14 make mechanical and electrical contact with connector pin 22 and connector ring 24 of adaptor connector terminal 20 or with connector elements 44 and 46 of lead connector terminal 42. According to one embodiment of the present invention, connector pin 22 and connector ring 24 are adapted for low-voltage coupling in port 14 while connector rings 26 and 28 are adapted for high-voltage coupling in port 14. According to alternate embodiments of the present invention any two of connector rings 24, 26, 28 and connector pin 22 may be eliminated and a remaining two be adapted for high-voltage coupling in port 14.

As illustrated in FIG. 1, adaptor 16 further includes a first receptacle port 32 and a second receptacle port 34 extending from a bifurcation 36 of an insulating body 30, which carries and electrically isolates conductors (not shown) extending from connector pin 22 and connector rings 24, 26, and 28 of adaptor connector terminal 20 to corresponding contacts included in receptacle ports 32 and 34. First port 32 and second port 34 are adapted to engage first lead connector 42 and second lead connector 62, respectively, providing electrical coupling for at least the high voltage electrodes of each lead. In some embodiments, second lead connector 62 conforms to the DF-1 connector standard.

Figure 2:
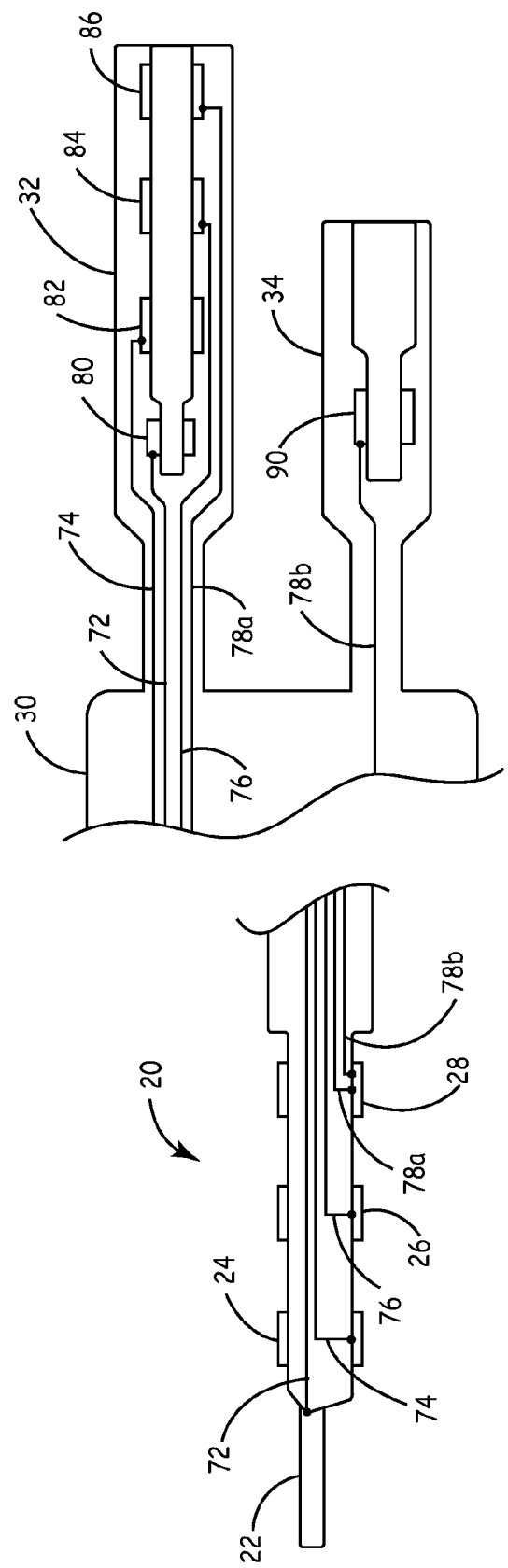
FIG. 2 is a sectional view of the adaptor of FIG. 1.

FIG. 2 is a sectional view of adaptor 16 wherein receptacle port 32 is shown to include low-voltage contacts 80 and 82 and high-voltage contacts 84 and 86 for providing electrical connection to lead connector elements 44, 46, 48, and 50 respectively (FIG. 1); contact 80 is coupled to connector pin 22 and via a conductor 72 and each of contacts 82, 84, and 86 are electrically coupled to connector rings 24, 26, and 28, respectively via conductors 74, 76, and 78a. Conductors 72, 74, 76 and 78a, extending through body 30 to adaptor connector terminal 20, are electrically isolated from one another.

FIG. 2 further illustrates receptacle port 34 including a high-voltage contact 90 for providing electrical connection to lead connector pin 64 of second lead 60. Contact 90 is electrically coupled to a conductor 78b, which is further coupled to connector ring 28 of connector terminal 20. Thus, according to some embodiments of the present invention, adaptor 16 performs as a signal splitter, providing common electrical connection for two high-voltage contacts 86 and 90 adapted to engage with high-voltage connector elements 50 and 64 located on separate leads 40 and 60, thereby enabling electrode 66 of second lead 60 to augment high-voltage therapy delivery of first lead 40.

Adaptor body 30 and external portions of receptacle 32 and 34 and connector assembly 20 may be formed from a biocompatible, insulating material known for use in manufacturing medical electrical leads. Appropriate materials include, but are not limited to, a polyurethane or silicone rubber. Conductors 72, 74, 76 and 78a may be provided as straight wire conductors, cabled conductors, coiled conductors or other types of conductors known for use in medical electrical leads or adaptors. Conductors 72, 74, 76, and 78a may extend through individual lumens formed within adaptor body 30 or may be individually insulated by a polymeric coating or tubing, such as PTFE or ETFE, and extend through a common central lumen formed within adaptor body 30.

While conductor 78b is shown coupled to contact 90 at a first end and connector ring 28 at a second end, the second end may alternatively be coupled to a node any where along conductor 78a. In this way, the high-voltage contact 84 of receptacle 32 and high-voltage contact 90 of receptacle 34 are both electrically coupled to the high-voltage connector ring 28 of adaptor connector terminal 20. In alternative embodiments, conductor 78b may be coupled to connector ring 26 or anywhere along conductor 76 such that a signal from connector ring 26 is split to high-voltage contact 84 of receptacle 32 via conductor 76 and to high-voltage contact 90 via conductor 78b.

Thus, an additional lead 60 including a high-voltage coil electrode 66 may be coupled to IMD 10 having a single connector port 14. Adaptor 16 allows placement of an additional, high-voltage lead in operative relation to the heart, without requiring a different IMD having an additional connector port, in order to achieve improved cardioversion or defibrillation thresholds when thresholds achieved with a single lead are unacceptably high.

It is recognized that in some embodiments according to the present invention a first lead may have only one high-voltage electrode, for example electrode 54 of lead 40 illustrated in FIG. 1; in this case, when a vector created between electrode 54 and can 11, acting as an electrode, does not provide an acceptably low defibrillation threshold a second lead including a high-voltage electrode, for example electrode 66 of lead 60, is coupled with the first lead to IMD 10 via adaptor 16 such that electrode 54 of the first lead is electrically coupled via contact 84 of first port 32, and electrode 66 of second lead 60 is coupled via contact 90 of second port 34 (FIG. 2). According to these embodiments contact 86 and conductor 78a are not necessary elements of adaptor 16. Additional alternate embodiments employ a switch as illustrated in FIG. 3.

Figure 3:
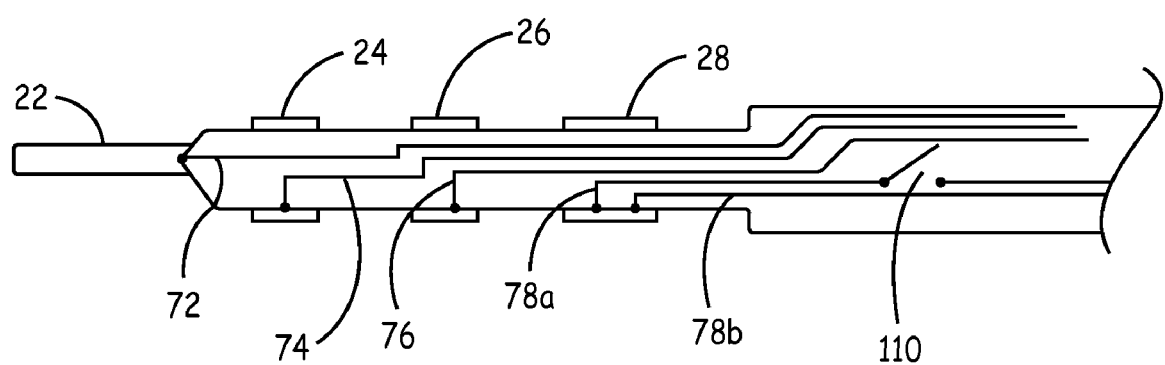
FIG. 3 is a sectional view of the connector terminal portion of an alternative embodiment of the adaptor of FIG. 2.

FIG. 3 is a sectional view of the connector terminal portion of an alternative embodiment of the adaptor of FIG. 2 wherein a switch 110 is provided to allow electrical decoupling of a receptacle contact. When defibrillation thresholds achieved using coil electrodes on a first lead, for example electrodes 54 and 52 of lead 40 shown in FIG. 1, are unacceptably high such that placement of a second high-voltage lead, for example lead 60, is required, it may be desirable to provide a high-voltage signal to the second lead without providing the same high-voltage signal to a coil electrode on the first lead. As such, switch 110 is provided between connector ring 28 and conductor 78a or anywhere along conductor 78a, which is coupled to contact 86 as shown previously in FIG. 2. Switch 110 may be an electrically-, mechanically-, or magnetically-actuated switch. With switch 110 normally closed, a signal delivered to connector ring 28 is split between contact 86 of receptacle 32 and contact 90 of receptacle 34 via conductors 78a and 78b, respectively. When switch 110 is opened, contact 86 is electrically disconnected from connector ring 28 such that a signal delivered to connector ring 28 is conducted only to contact 90 via conductor 78b.

Figure 4:
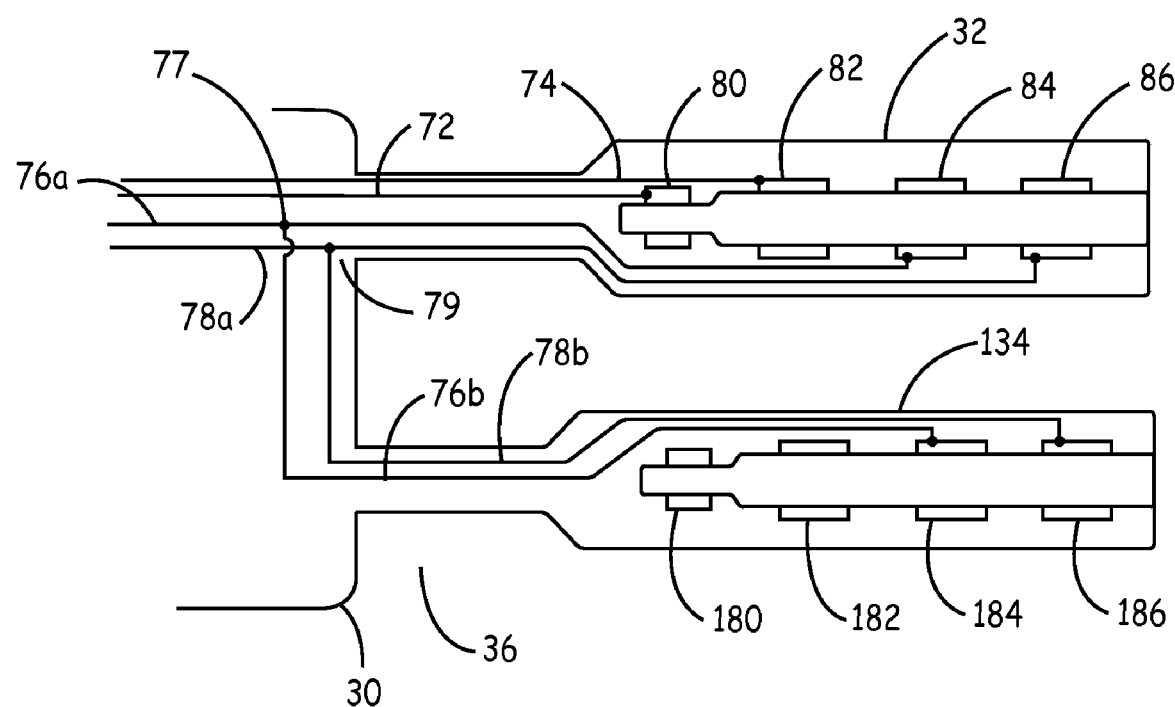
FIG. 4 is a sectional view of an alternative embodiment of the adaptor of FIG. 2.

FIG. 4 is a sectional view of an alternative embodiment of the adaptor of FIG. 2 wherein a second port 134 is adapted to engage another multi-polar lead including a connector terminal similar to that of first lead 40 illustrated in FIG. 1. According to this embodiment, signals delivered to two high-voltage connector rings are split to contacts engaging with connector elements of two separate leads. As such, receptacle 134 includes four contacts 180, 182, 184, and 186. Conductor 78b is shown in FIG. 4 to be coupled at one end to high-voltage contact 186 and at the other end to conductor 78a at node 79, which may be located anywhere along the length of conductor 78a. Conductor 78a is further coupled to connector ring 28 of adaptor connector terminal 20 (FIGS. 2 and 3). Conductor 76b is coupled at one end to high-voltage contact 184 and at the other end to conductor 76a at node 77, which may be located anywhere along the length of conductor 76a. Conductor 76a is further coupled to connector ring 26 on adaptor connector terminal 20 (FIGS. 2 and 3). Thus, both high-voltage connector rings 26 and 28 of adaptor connector terminal 20 are coupled to high-voltage contacts in receptacles 32 and 134 allowing connection of two leads, each having two high-voltage coil electrodes, to a single connection port of an IMD. Signals delivered to connector ring 26 are split between contacts 84 and 184 and signals delivered to connector ring 28 are split between contacts 86 and 186. In alternative embodiments, conductors 76*b* and 78*b* may be coupled directly to connector rings 26 and 28 of connector terminal 20 rather than to nodes 77 and 79 as shown in FIG. 4. Contacts 180 and 182 may be left inactive as shown in FIG. 4, i.e., having no electrical connection to conductors extending to adaptor connector terminal 20. In other embodiments, additional conductors may be provided for coupling additional contacts that may be present in receptacle 134 to connector elements included in connector terminal 20.

Figure 5:
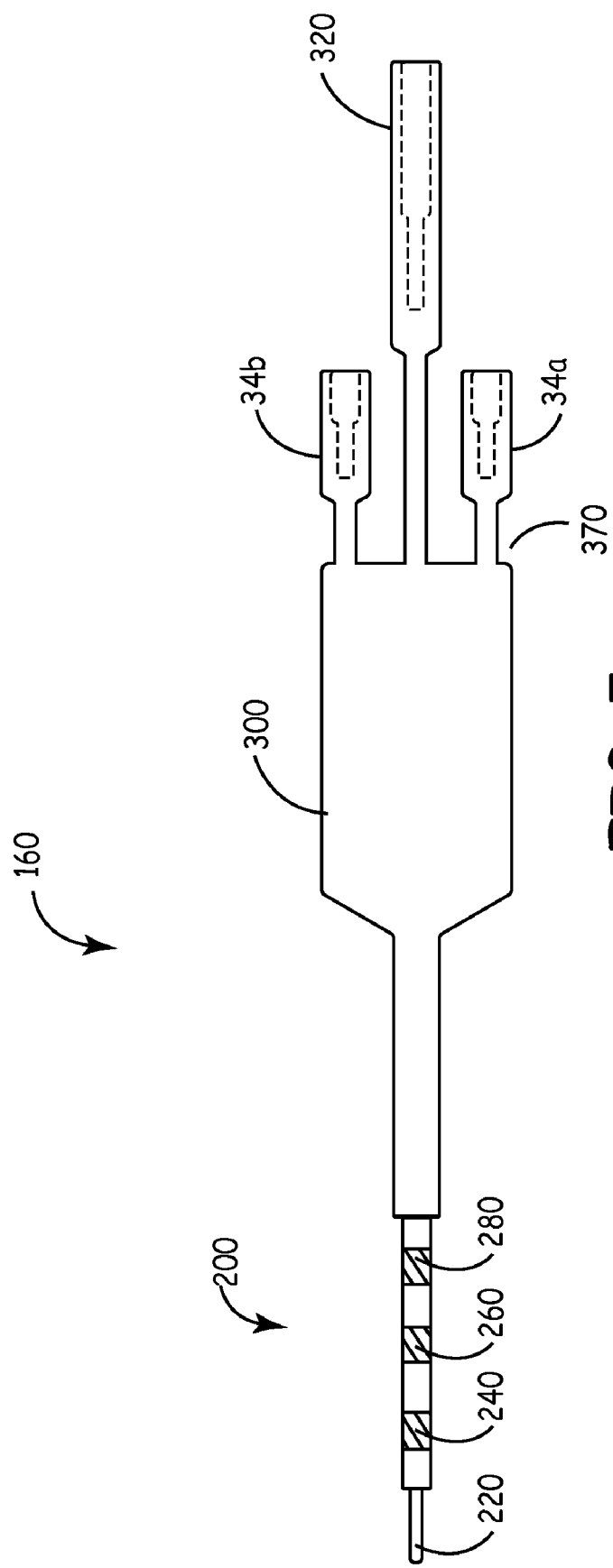
FIG. 5 is a plan view of a trifurcated adaptor according to an alternate embodiment of the present invention.

FIG. 5 is a plan view of yet another embodiment of an adaptor 160 provided for splitting signals delivered to two high-voltage contacts engaging connector elements located on a first lead, for example connector elements 48 and 50 of lead 40 illustrated in FIG. 1, and two additional high-voltage contacts located in two separate ports 34*a* and 34*b* for engaging connector elements of two separate leads, for example 64 of lead 60. FIG. 5 illustrates a connector terminal 20 of adaptor 160 extending from an adaptor body 300 and including a connector pin 220 and connector rings 240, 260 and 280. Three receptacle ports 32, 34*a* and 34*b* extend from a trifurcation 370 at the opposite end of adaptor body 300.

Figure 6:
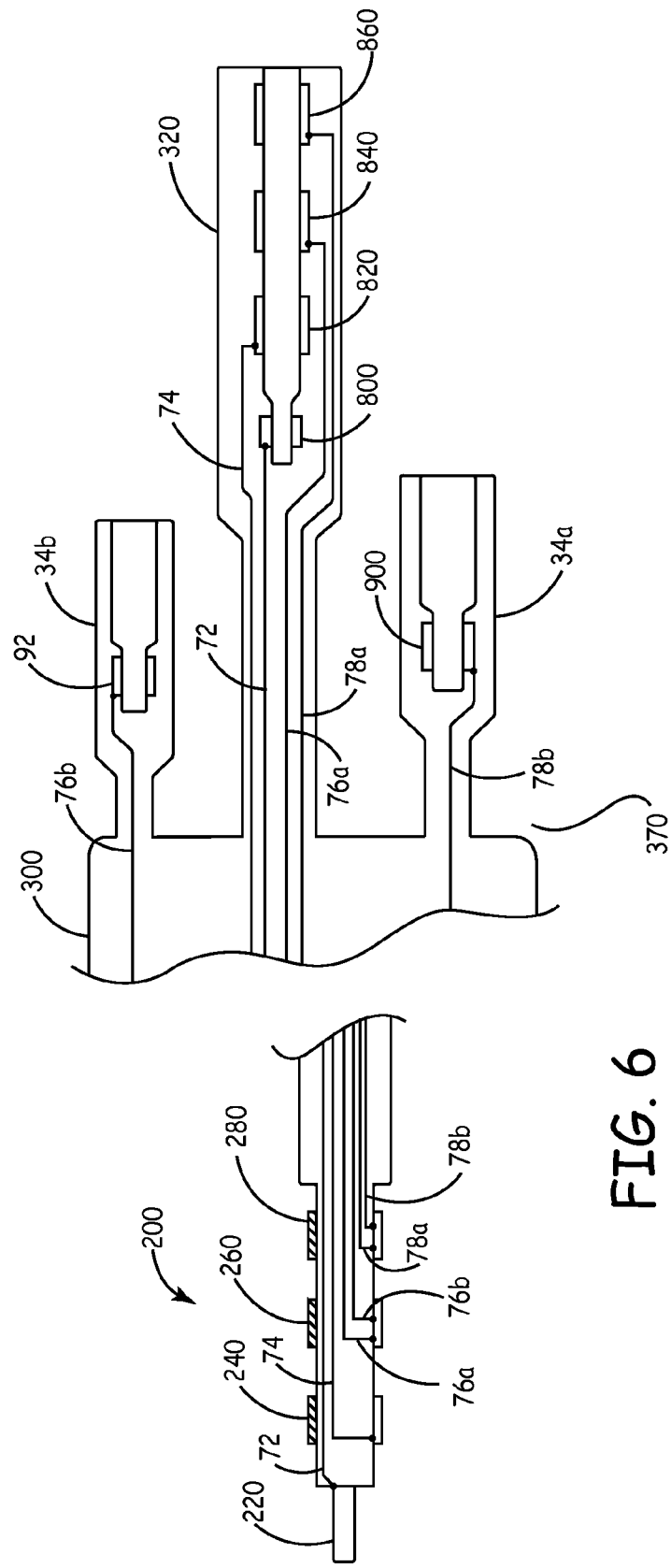
FIG. 6 is a sectional view of the adaptor of FIG. 5.

As shown in more detail in the sectional view of FIG. 6, receptacle port 320 includes include low-voltage contacts 800 and 820 and high-voltage contacts 840 and 860 for providing electrical connection to lead connector elements 44, 46, 48, and 50 respectively (FIG. 1); contact 800 is coupled to connector pin 220 and via a conductor 72 and each of contacts 820, 840, and 860 are electrically coupled to connector rings 240, 260, and 280, respectively via conductors 74, 76*a*, and 78*a*. Conductors 72, 74, 76*a* and 78*a*, extending through body 30 to adaptor connector terminal 20, are electrically isolated from one another.

FIG. 6 further illustrates receptacle ports 34*a* and 34*b* each including a single, high-voltage contact 900 and 92, respectively. Ports 34*a* and 34*b* may be adapted to receive standard DF-1 lead connectors. Conductor 78*b* is coupled between contact 900 of receptacle port 34*a* and connector ring 280 of adaptor connector terminal 200 such that signals delivered to connector ring 280 are split between contact 860 of receptacle port 320 and contact 900 via conductors 78*a* and 78*b*, respectively. Conductor 76*b* is coupled between contact 920 of receptacle port 34*b* and connector ring 260 of adaptor connector terminal 200. Signals delivered to connector ring 260 are split between contact 840 of receptacle port 320 and contact 92 via conductors 76*a* and 76*b*, respectively. Adaptor 160 of FIGS. 5 and 6 thus allows connection of two additional high-voltage leads to an IMD having a single connection port, for example IMD 10 shown in FIG. 1.

Figure 7:
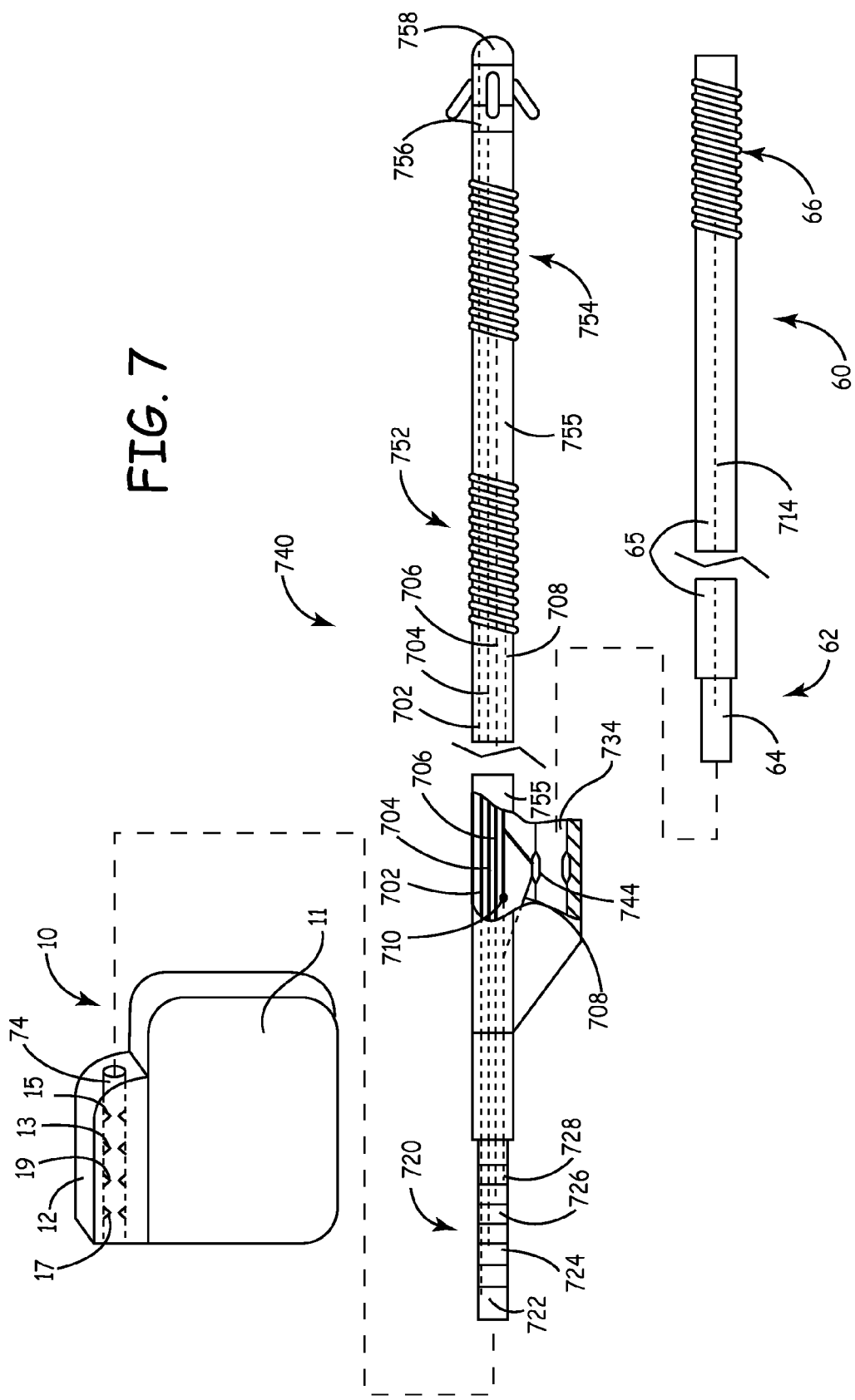
FIG. 7 is plan view of a medical system according to an alternate embodiment of the present invention.

FIG. 7 is plan view of a medical system according to an alternate embodiment of the present invention wherein means for connecting two medical electrical leads to single port 14 of IMD 10 includes an auxiliary port 734 built into a first lead 740. FIG. 7 illustrates first medical electrical lead 740 including a tip electrode 758 and a ring electrode 756, which provide low-voltage therapy, for example pacing and sensing, and two coil electrodes 752 and 754, which provide high voltage therapy, for example defibrillation. Each electrode 752, 754, 756, and 758 is electrically coupled to a corresponding connector element 728, 726, 724, and 722, respectively, located on a lead connector terminal 720 via electrically isolated conductors 708, 706, 704, and 702, respectively, carried by a lead body 755. Conductors 708, 706, 704, and 702 may be straight wire conductors, cabled conductors, coiled conductors or other types of conductors known for use in medical electrical leads or adaptors and may extend through individual lumens formed within lead body 755 or may be individually insulated by a polymeric coating or tubing, such as PTFE or ETFE, and extend through a common central lumen formed within lead body 755. Connector terminal 720 is adapted to engage within connector port 14 of connector header 12 of IMD 10, which is described herein in conjunction with FIG. 1.

FIG. 7 further illustrates auxiliary port 734 of first lead 740 including a connector contact 744 coupled to connector element 728 via conductor 708. Connector contact 744 may be a spring contact or setscrew contact, both types being well known to those skilled in the art. According to embodiments of the present invention auxiliary port 734 is adapted to engage connector terminal 62 of second lead 60 in order to electrically couple electrode 66 of second lead 60 to connector element 728 of connector terminal 720, via contact between connector contact 744 and connector pin 64, which is coupled to electrode 66 by conductor 714. As previously described in conjunction with FIG. 1, electrode 66 of second lead 60 may be implanted in a position to create a more effective defibrillation vector with an electrode or electrodes of a first lead, which in this case are electrodes 752 and 754 of first lead 740, in order to reduce a defibrillation threshold.

FIG. 7 also illustrates a switch 710, which is adapted to reversibly decouple electrode 752 from connector element 728 when only electrode 66 of second lead, coupled via port 734, and electrode 754 of first lead provide a desired defibrillation threshold. With switch 110 normally closed, a defibrillation pulse delivered from IMD 10, via connector element 728 of connector terminal 720, is split between electrode 752 of first lead and electrode 66 of second lead, while, when switch is open, the defibrillation pulse is sent only to electrode 66. Switch 710 may be an electrically-, mechanically-, or magnetically-actuated switch.

Although FIG. 7 illustrates conductor 708 coupling connector contact 744 and electrode 752 to connector element 728, in alternate embodiments according to the present invention, a first lead does not include electrode 752 so that conductor 708 only couples contact 744 to connector element 728. Furthermore, in additional embodiments, first lead 740 does not include electrode 756 and associated conductor 704 and connector element 724, in which case electrode 758 operates in a unipolar pace/sense mode or in an integrated bipolar pace/sense mode in conjunction with electrode 754, both modes being well known to those skilled in the art. In yet another embodiment first lead 740 does not include coil electrodes 752 and 754, in which case one of conductors 706 and 708 is not included and the other only couples contact 744 to one of connector elements 726 and 728, providing means to augment a pace/sense system with coil electrode 66 via engagement of connector terminal 62 in port 734; electrode 66 forming a defibrillation vector with either can 11 or a coil electrode on yet another lead (not shown) included in the system.

Figure 8:
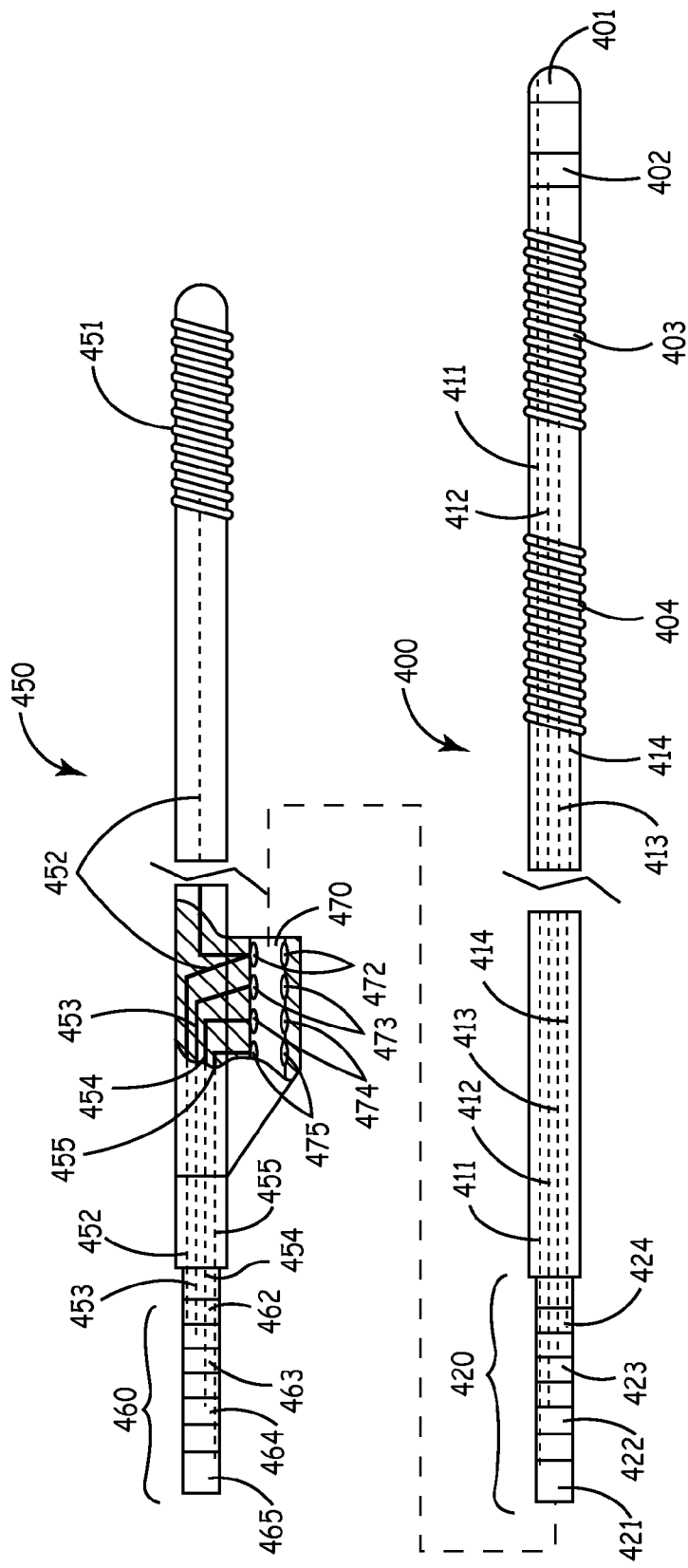
FIG. 8 is a plan view of a medical system according to yet another alternate embodiment of the present invention.

FIG. 8 is a plan view of a medical system according to yet another alternate embodiment of the present invention. FIG. 8 illustrates a first lead 450 including a high-voltage electrode 451, a connector terminal 460 and an auxiliary port 470; electrode 451 is shown coupled, via a first insulated conductor 452, to both a connector element 462 of connector terminal 460 and to a connector contact 472 of auxiliary port 470. Connector terminal 460 is adapted to engage within connector port 14 of connector header 12 of IMD 10 (FIGS. 1 and 7), which is described herein in conjunction with FIG. 1. FIG. 8 further illustrates first lead 450 including a second, a third and a fourth insulated conductor 453, 454, and 455 coupling connector elements 463, 464, and 465 of connector terminal 460 to connector contacts 473, 474, and 475, respectively, included in port 470. According to embodiments of the present invention, port 470 is adapted to engage a connector terminal of a second lead, for example a connector terminal 420 of a second lead 400 illustrated in FIG. 8, thereby supplementing second lead 400 with an additional high-voltage electrode, i.e. electrode 451, to create a more effective defibrillation vector, as previously described. In the exemplary system illustrated by FIG. 8, second lead 400 includes a tip electrode 401 and a ring electrode 402, adapted for pacing and sensing, and a first high-voltage electrode 403 and a second high-voltage electrode 404; each electrode 401, 402, 403 and 404 are coupled to connector elements 421, 422, 423 and 424, respectively, of connector terminal 420 via insulated conductors 411, 412, 413 and 414, respectively. According to embodiments of the present invention, connector terminal 420 of second lead 400, like connector terminal 460 of first lead 450, is adapted to engage within connector port 14 of connector header 12 of IMD 10, however, when connector terminal 420 of second lead is engaged within port 470 of second lead, connector elements 421, 422, 423 and 424 are coupled to connector elements 465, 464, 463 and 462, respectively, which are then engaged by connector port 14 of IMD 10.

Although FIG. 8 illustrates second lead 400 as a quadripolar lead including electrodes 401, 402, 403 and 404 wherein additional electrode 451 is joined in common with high-voltage electrode 404 via port 470, in alternate embodiments according to the present invention, a second lead may be a tripolar lead which does not include high-voltage electrode 404. In additional embodiments a second lead may not include low-voltage electrode 402; further combinations of electrodes understood by those skilled in the art are within the spirit of the present invention.

Illustrative embodiments of systems incorporating means for connecting multiple high-voltage leads to an IMD having a single connection port have been described herein. While the present invention has been described in the context of specific embodiments, these embodiments are intended to be exemplary and are not intended to limit the scope, applicability, or configuration of the invention in any way. It should be understood that various changes may be made in the function and arrangement of elements described in exemplary embodiments without departing from the scope of the invention as set forth in the appended claims.

What is claimed is:

1. A medical system, comprising:
a first lead including a first electrode, a second electrode, a first insulated conductor, a second insulated conductor, a connector terminal, and an auxiliary connector port; the auxiliary connector port including a connector contact; and the lead connector terminal including a first connector element electrically coupled to the first electrode via the first conductor, a second connector element electrically coupled to the connector contact of the auxiliary port via the second conductor, and a third connector element;
a second lead including an electrode adapted for high-voltage therapy, an insulated conductor, and a connector terminal; the connector terminal of the second lead including a connector element electrically coupled to the electrode via the conductor; and
an IMD including a connector port including a first connector and a second connector;
wherein, the first, second and third connector elements of the first lead are adapted to make an electrical connection within the connector port of the IMD;
the auxiliary port of the first lead is adapted to engage the connector terminal of the second lead thereby electrically coupling the connector element of the second lead to the second connector element of the connector terminal of the first lead via the connector contact; and
the connector port of the IMD is adapted to engage the connector terminal of the first lead thereby electrically coupling the first connector element of the first lead, via the first connector, and the second connector element of the first lead, via the second connector, to the IMD.

2. The medical system of claim 1, wherein the first electrode is adapted for high-voltage therapy.

3. The medical system of claim 2, wherein:
the first lead further includes a third insulated conductor electrically coupling the third connector element of the connector terminal of the first lead to the second electrode of the first lead;
the second electrode of the first lead is adapted for low-voltage therapy; and
the connector port of the IMD further includes a third connector electrically coupling the third connector element of the connector terminal of the first lead to the IMD when the connector port of the IMD engages the connector terminal of the first lead.

4. The medical system of claim 2 wherein the second electrode of the first lead is adapted for high-voltage therapy and the second conductor of the first lead further electrically couples the second electrode to the second connector element of the connector terminal of the first lead.

5. The medical system of claim 4, wherein the first lead further includes a switch adapted to reversibly disconnect the coupling of the second conductor to the second electrode of the first lead.

6. The medical system of claim 4, wherein
the first lead further includes a third electrode adapted for low-voltage therapy and a third insulated conductor;
the connector terminal of the first lead further includes a fourth connector element electrically coupled to the third electrode via the third insulated conductor; and
the connector port of the IMD further includes a third connector coupling the fourth connector element of the connector terminal of the first lead to the IMD when the connector port of the IMD engages the connector terminal of the first lead.

7. A medical electrical lead, comprising:
a first electrode;
a second electrode;
a first insulated conductor;
a second insulated conductor;
an auxiliary connector port including a connector contact adapted to electrically couple an electrode of a second lead; and
a connector terminal including a first connector element electrically coupled to the first electrode via the first conductor, a second connector element electrically coupled to the connector contact of the auxiliary port via the second conductor, and a third connector element;
wherein the first, second and third connector elements are adapted to make an electrical connection.

8. The medical electrical lead of claim 7, wherein the first electrode is adapted for high-voltage therapy.

9. The medical electrical lead of claim 8, further comprising a third insulated conductor electrically coupling the third connector element of the connector terminal to the second electrode; and wherein the second electrode is adapted for low-voltage therapy.

10. The medical electrical lead of claim 8, wherein the second electrode is adapted for high-voltage therapy and the second conductor further electrically couples the second electrode to the second connector element of the connector terminal.

11. The medical electrical lead of claim 10, further comprising a switch adapted to reversibly disconnect the coupling of the second conductor to the second electrode.

12. The medical electrical lead of claim 10, further comprising:
a third electrode adapted for low-voltage therapy; and
a third insulated conductor; wherein
the connector terminal further includes a fourth connector element electrically coupled to the third electrode via the third insulated conductor.

13. A medical system, comprising:
a first lead including an electrode adapted for high-voltage therapy, a first insulated conductor, a second insulated conductor, a third insulated conductor, a connector terminal, and an auxiliary connector port; the auxiliary connector port including a first connector contact and a second connector contact and the lead connector terminal including a first connector element coupled to the first electrode via the first conductor, a second connector element coupled to the first connector contact of the auxiliary port via the second conductor and a third connector element coupled to the second connector contact via the third conductor;
a second lead including a first electrode adapted for high-voltage therapy, a second electrode adapted for low-voltage therapy, a first insulated conductor, a second insulated conductor and a connector terminal; the connector terminal of the second lead including a first connector element coupled to the first electrode of the second lead via the first conductor of the second lead and a second connector element coupled to the second electrode of the second lead via the second conductor of the second lead; and
an IMD including a connector port including a first connector, a second connector and a third connector;
wherein, the auxiliary port of the first lead is adapted to engage the connector terminal of the second lead thereby coupling the first connector element of the second lead to the second connector element of the connector terminal of the first lead via the first connector contact and coupling the second connector element of the second lead to the third connector element of the first lead via the second connector contact; and
the connector port of the IMD is adapted to engage the connector terminal of the first lead thereby coupling the first connector element of the first lead, via the first connector, the second connector element of the first lead, via the second connector, and the third connector element of the first lead, via the third connector, to the IMD.

14. The medical system of claim 13, wherein:
the auxiliary port of the first lead further includes a third connector contact and the first connector element of the first lead is further coupled to the third connector contact via the first conductor of the first lead;
the second lead further includes a third electrode adapted for high voltage therapy and a third insulated conductor;
the connector terminal of the second lead further includes a third connector element coupled to the third electrode of the second lead via the third insulated conductor of the second lead; and
the auxiliary port is further adapted to couple the third connector element of the second lead to the first connector element of the first lead via the third connector contact.

15. The medical system of claim 14, wherein
the first lead further includes a fourth insulated conductor;
the auxiliary port of the first lead further includes a fourth connector contact;
the connector terminal of the first lead further includes a fourth connector element coupled to the fourth connector contact via the fourth conductor of the first lead;
the second lead further includes a fourth electrode adapted for low-voltage therapy and a fourth insulated conductor;
the connector terminal of the second lead further includes a fourth connector element coupled to the fourth electrode via the fourth conductor;
the auxiliary port of the first lead is further adapted to couple the fourth connector element of the second lead to the fourth connector element of the first lead via the fourth connector contact; and
the connector port of the IMD further includes a fourth connector coupling the fourth connector element of the connector terminal of the first lead to the IMD when the connector port of the IMD engages the connector terminal of the first lead.

16. A supplemental defibrillation lead, comprising:
a high-voltage electrode;
a first insulated conductor;
a second insulated conductor;
a third insulated conductor;
an auxiliary connector port including a first connector contact adapted to electrically couple a high-voltage electrode of a second lead and a second connector contact adapted to electrically couple a low-voltage electrode of the second lead; and
a connector terminal including a first connector element electrically coupled to the high-voltage electrode of the defibrillation lead via the first conductor, a second connector element electrically coupled to the first connector contact of the auxiliary port via the second conductor and a third connector element electrically coupled to the second connector contact of the auxiliary port via the third conductor.

17. The defibrillation lead of claim 16, wherein:
the auxiliary connector port further includes a third connector contact adapted to electrically engage a second high-voltage electrode of the second lead; and
the first conductor further electrically couples the first connector element to the third connector contact.

18. The defibrillation lead of claim 17 further comprising a fourth insulated conductor and wherein:
the auxiliary port further includes a fourth connector contact adapted to electrically couple a second low-voltage electrode of the second lead; and
the connector terminal further includes a fourth connector element electrically coupled to the fourth connector contact via the fourth conductor.

* * * * *